US007893088B2

(12) United States Patent
Ray et al.

(10) Patent No.: US 7,893,088 B2
(45) Date of Patent: Feb. 22, 2011

(54) 6-SUBSTITUTED ISOQUINOLINE DERIVATIVES

(75) Inventors: Peter Christopher Ray, Newhouse (GB); Steven Laats, Newhouse (GB); John Richard Morphy, Newhouse (GB); Brad Sherborne, Newhouse (GB)

(73) Assignee: N.V. Organon, Oss (NL)

( * ) Notice: Subject to any disclaimer, the term of this patent is extended or adjusted under 35 U.S.C. 154(b) by 686 days.

(21) Appl. No.: 11/839,703

(22) Filed: Aug. 16, 2007

(65) Prior Publication Data

US 2008/0045566 A1 Feb. 21, 2008

Related U.S. Application Data

(60) Provisional application No. 60/838,719, filed on Aug. 18, 2006.

(30) Foreign Application Priority Data

Aug. 18, 2006 (EP) .................................. 06119142

(51) Int. Cl.
*C07D 217/00* (2006.01)
*A61K 31/47* (2006.01)
(52) U.S. Cl. ...................... 514/309; 546/141
(58) Field of Classification Search ........................ None
See application file for complete search history.

(56) References Cited

U.S. PATENT DOCUMENTS

| 7,618,985 B2 | 11/2009 | Ray |
| 2006/0167043 A1 | 7/2006 | Iwakubo et al. |
| 2007/0135479 A1 | 6/2007 | Ray |

FOREIGN PATENT DOCUMENTS

| EP | 1403255 | 3/2004 |
| EP | 1541559 | 6/2005 |
| EP | 1550660 | 7/2005 |
| WO | WO 2004/009555 | 1/2004 |
| WO | WO 2004/024717 | 3/2004 |
| WO | WO 2006/051290 | 5/2006 |
| WO | WO 2007/012422 | 2/2007 |

OTHER PUBLICATIONS

Elliot et.al., "2-(Aryloxymethyl) Azacyclic Analogues As Novel Nicotinic Acetylcholine Receptor (nAChR) Ligands," *Bioorg. Med. Chem. Lett.* 6 (1996) 2283-2288.
Hendrickson et.al., "An Efficient Synthesis of Substituted Isoquinolines," *J. Org. Chem.* 48 (1983) 3344-3346.
Hirooka et.al., "Therapeutic Potential of Rho-Kinase Inhibitors in Cardiovascular Diseases," *Am. J. Cardiovasc. Drugs* 5 (2005) 31-39.
Hu, E. et al.,"Rho Kinase as Potential Therapeutic Target for Cardiovascular Diseases . . . ," *Expert Opinion Ther. Targets*, 9(4), 2005, 715-736.
Kende et.al., "A Regiospecific Synthesis of (±)-Decarbomethoxyaklavinone," *Tetrahedron Lett.* 22 (1981) 1779-1782.
McOmie, J.F.W., et al., "3,3'-Dihydroxybiphenyl," *Org. Synth., Collect. vol. V*, 1973, 412-414.
Mueller, B. et al., "Rho Kinase, A Promising Drug Target for Neurological Disorders," *Nature Reviews Drug Discovery*, 4, 2005, 387-398.
Newman, M.S. et al., "The Conversion of Phenols to Thiophenols via Dialkylthiocarbamates," *J. Org. Chem.* 31, 1966, 3980-3984.
Wisniewski, K. et al., "Applications of the Mitsunobu Reaction in Peptide Chemistry," *J.Pept. Sc. 4*, 1998, 1-14.
Wolfe, J.P., et al., "Simple, Efficient Catalyst System for the Palladium-Catalyzed Amination of Aryl Chlorides, Bromides, and Triflates," *J. Org. Chem.* 65, 2000, 1158-1174.
Chen, P., et. al. Identification of Novel and Potent Isonquinoline Aminooxazole-Based IMPDH Inhibitors, Bioorg. Med. Chem, Lett. 13,2003, 1345-1348.
Written Opinion for International Application No. PCT/EP2006/069392 mailed Mar. 1, 2007.
International Search Report for PCT/EP2006/069392 mailed Mar. 1, 2007.
International Search Report for PCT/US2007/058593 mailed Jul. 25, 2008.
Written Opinion for International Application No. PCT/US2007/058593 mailed Jul. 25, 2008.

*Primary Examiner*—Zinna N Davis
(74) *Attorney, Agent, or Firm*—Susan L. Hess

(57) ABSTRACT

The present invention relates to 6-substituted isoquinoline derivatives having the general Formula I

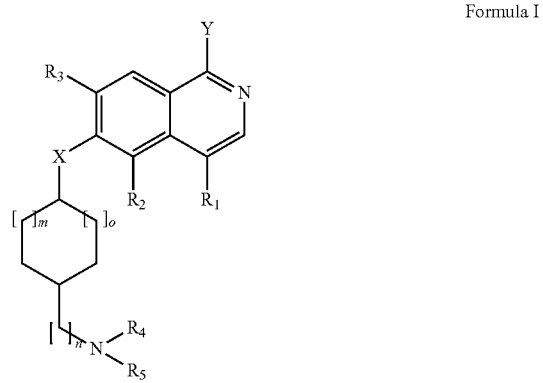

Formula I wherein X is O, S or NH; Y is OH or $NH_2$; m is 0, 1 or 2; n is 0 or 1; o is 0 or 1; $R_1$ is H, when Y is $NH_2$; or $R_1$ is H, $(C_{1-4})$alkyl or halogen, when Y is OH; $R_2$ and $R_3$ are independently H, $(C_{1-4})$alkyl or halogen; $R_4$ is H or $(C_{1-6})$alkyl, optionally substituted with halogen, $(C_{3-7})$cycloalkyl, $(C_{6-10})$ aryl or a saturated 5- or 6-membered heterocyclic ring comprising 1-3 heteroatoms independently selected from O, S and N, the $(C_{6-10})$aryl and heterocyclic ring being optionally substituted with $(C_{1-4})$alkyl, $(C_{1-4})$alkyloxy or halogen; $R_5$ is H or $(C_{1-4})$alkyl; or a pharmaceutically acceptable salt thereof, with the proviso that the compounds of Formula I wherein X is O, Y is OH , n is 0 and m+o=2 are excluded, to pharmaceutical compositions comprising the same, as well as to the use of said 6-substituted isoquinoline derivatives for the preparation of a medicament for the treatment of ROCK-I related disorders such as glaucoma, hypertension and atherosclerosis.

12 Claims, No Drawings

6-SUBSTITUTED ISOQUINOLINE DERIVATIVES

This invention relates to 6-substituted isoquinoline derivatives, to pharmaceutical compositions comprising the same, as well as to the use of these derivatives for the preparation of a medicament for the treatment of ROCK-I related disorders, such as glaucoma, hypertension and atherosclerosis.

The vast majority of signal transduction pathways are controlled by the reversible phosphorylation of proteins. There are currently approximately 500 known protein kinases, which are responsible for phosphorylation of proteins and thus the control of cellular signalling events. Many diseases are associated with abnormal cellular responses triggered by protein kinase-mediated events and there has been a substantial effort in medicinal chemistry to find protein kinase inhibitors that are effective as therapeutic agents. The protein kinase family is classified into tyrosine kinases and serine/threonine kinases, based on the amino acid residue they phosphorylate. Recently, histidine kinases (which phosphorylate the imidazole nitrogen on a histidine residue) have also been discovered.

The AGC sub-family of kinases belong to the serine and threonine family of kinases and participate in a variety of signalling processes. This sub-family include Rho-associated coiled coil forming protein kinase (ROCK). Two ROCK isoforms have been reported: ROCK-I/ROKβ/p160ROCK and ROCKII/ROKx/Rho-kinase. These two proteins share 65% similarity at the amino-acid level and 92% in their kinase domains. ROCK-I and ROCK-II were among the first effectors of the small GTPases of the Rho family to be discovered. The Rho-ROCK signalling pathway controls cell shape adhesion, contractility, cell motility and invasion. First generation inhibitors Y-27632 and Fasudil have been used extensively to elucidate the biological roles of ROCK-I and ROCK-II in various diseases and or disorders. As a result, ROCK inhibitors have been suggested to have therapeutic value in bronchial asthma, cerebral vasospasm, coronary vasospasm, erectile dysfunction, glaucoma, preterm labour, vascular smooth muscle proliferation, myocardial hypertrophy, malignoma, ischemia/reperfusion-induced injury, endothelial dysfunction, Crohn's disease and colitis, neurite outgrowth, Raynaud's Disease, angina, Alzheimer's diseases, benign prostatic hyperplasia, neuropathic pain, hypertension and atherosclerosis (Mueller B. K et al, *Nature Reviews Drug Discovery* 4, 387-398 (2005); Hirooka Y. and Shimokawa H. *Am. J. Cardiovasc. Drugs* 5(1) 31-39 (2005); Hu E. and Lee D. *Current Opinion Ther. Targets* 9(4), 715-736 (2005)).

5-Substituted isoquinoline derivatives have been disclosed as inhibitors of the Rho/Rho kinase pathway in the International Patent Application WO 2004/009555 (EP 1541559; Asahi Kasei Pharma Corporation). N-substituted 5-isoquinolylamine derivatives were disclosed as Rho kinase inhibitors in the International Patent Application WO 2004/024717 (EP 1550660; Kirin Brewerey Kabashiki Kaisha). Quinazolone compounds have been disclosed that inhibit or modulate the activity of protein kinase A (PKA) and protein kinase B (PKB) in the International Patent Application WO 2006/051290. There remains a need for additional compounds useful in the treatment of Rho kinase mediated diseases such as glaucoma, hypertension and atherosclerosis.

To that aim the present invention provides 6-substituted isoquinoline derivatives having the general Formula I

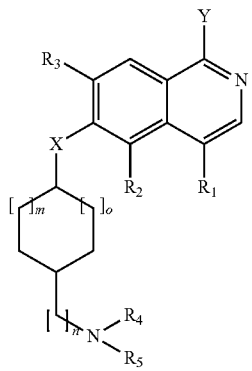

Formula I wherein
X is O, S or NH;
Y is OH or $NH_2$;
m is 0, 1 or 2;
n is 0 or 1;
o is 0 or 1;
$R_1$ is H, when Y is $NH_2$; or $R_1$ is H, $(C_{1-4})$alkyl or halogen, when Y is OH;
$R_2$ and $R_3$ are independently H, $(C_{1-4})$alkyl or halogen;
$R_4$ is H or $(C_{1-6})$alkyl, optionally substituted with halogen, $(C_{3-7})$cycloalkyl, $(C_{6-10})$aryl or a saturated 5- or 6-membered heterocyclic ring comprising 1-3 heteroatoms independently selected from O, S and N, the $(C_{6-10})$aryl and heterocyclic ring being optionally substituted with $(C_{1-4})$alkyl, $(C_{1-4})$alkyloxy or halogen;
$R_5$ is H or $(C_{1-4})$alkyl; or a pharmaceutically acceptable salt thereof; with the proviso that the compounds of Formula I wherein X is O, Y is OH , n is 0 and m+o=2 are excluded.

The proviso relates to the recent disclosure in the International Patent Application WO 2007/012422 (Sanofi-Aventis Deutsland GMBH) of cyclohexylamine isoquinolone derivatives as Rho-kinase inhbitors.

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl.

Likewise, the term $(C_{1-6})$alkyl as used in the definition of Formula I means a branched or unbranched alkyl group having 1-6 carbon atoms, like hexyl, pentyl, isopentyl, butyl, isobutyl, tertiary butyl, propyl, isopropyl, ethyl and methyl.

The term $(C_{3-7})$cycloalkyl means a cycloalkyl group having 3-7 carbon atoms, like cycloheptyl, cyclohexyl, cyclopentyl, cyclobutyl and cyclopropyl.

In the term $(C_{1-4})$alkyloxy, $(C_{1-4})$alkyl has the meaning as defined above.

The term halogen means F, Cl, Br or I.

The term $(C_{6-10})$aryl means an aromatic ring system having 6-10 carbon atoms, like phenyl of naphthyl.

In the definition of Formula I the saturated 5- or 6-membered heterocyclic ring comprising 1-3 heteroatoms selected from O, S and N is exemplified by tetrahydropyranyl, tetrahydrofuranyl, tetrahydrothiopyranyl, tetrahydrothienyl, pyrrolidinyl, piperidinyl, morpholinyl and thiomorpholinyl.

There is a preference for 6-substituted isoquinolin derivatives of Formula I wherein Y is OH. It is understood that such compounds can also occur in the tautomeric amide O-form and may therefore also be described as 2H-isoquinolin-1-ones:

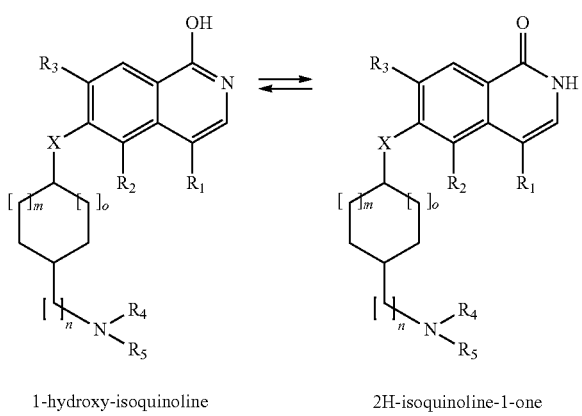

1-hydroxy-isoquinoline ⇌ 2H-isoquinoline-1-one

Further preferred compounds of Formula I are those wherein X is O. In the more preferred compounds of the invention for Formula I, $R_1$ and $R_3$ are independently H, methyl or halogen, and $R_2$ is H.

Specifically preferred 6-substituted isoquinoline derivatives of the invention are:
- (1S, 3R)-6-(3-aminomethylcyclopentyloxy)-2H-isoquinolin-1-one;
- 6-(4-aminomethylcyclohexyloxy)-2H-isoquinolin-1-one;
- (1R, 3R)-6-(3-aminomethylcyclopentyloxy)-2H-isoquinolin-1-one;
- (1R,3S)-6-(3-aminomethylcyclopentyloxy)-2H-isoquinolin-1-one;
- (1S, 3S)-6-(3-aminocyclopentyloxy)-2H-isoquinolin-1-one;
- (1R, 3R)-6-(3-aminocyclopentyloxy)-2H-isoquinolin-1-one;
- cis-6-(4-aminocyclohexylsulfanyl)isoquinolin-1-ylamine;
- (1S, 3S)-6-(3-aminomethylcyclopentyloxy)-2H-isoquinolin-1-one; and pharmaceutically acceptable salts thereof.

Compounds of Formula I may be prepared from a compound of Formula II, wherein $R_1$-$R_3$, $R_5$, X, Y, m, n and o have the previously defined meaning, any reactive group in Y optionally carrying a protecting group, and Pg is an N-protecting group, by removal of said N-protecting group (Pg) and subsequent N-alkylation with an appropriate halide of Formula $R_4$-Hal, or by reductive amination with an appropriate aldehyde derived from group $R_4$, after which any remaining protecting group is removed.

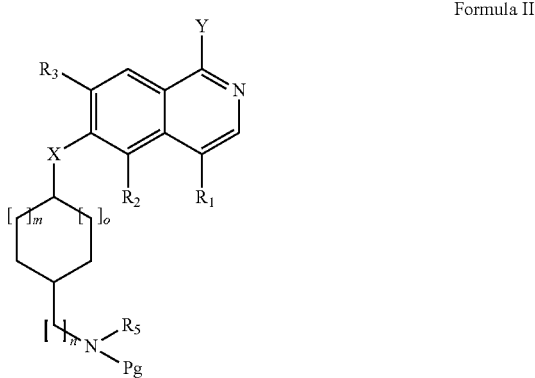

Formula II

The term N-protecting group means a group commonly used for the protection of an amino group, like the alloxycarbonyl (Alloc) group, the tert-butyloxycarbonyl (Boc) group, the benzyloxycarbonyl (Z) group or the 9-fluorenylmethyloxycarbonyl (Fmoc) group. Removal of these and other protecting groups can take place in different ways, depending on the nature of those protecting groups. An overview of protecting groups and methods for their removal is given in T. W. Greene and P. G. M. Wuts, Protective Groups in Organic Synthesis, $2^{nd}$ edition, 1991, John Wiley & Sons, Inc.

Compounds of Formula II can be prepared from the coupling of a compound of Formula III, wherein $R_1$-$R_3$, X and Y have the meaning as previously defined, with a compound of Formula IV, wherein m, n, o, $R_5$ and Pg have the previously given meaning and wherein L is OH, using standard Mitsunobu conditions [R. L. Elliot, H. Kopecka, D. E. Gunn, H. N. Lin and D. S. Garvey, *Bioorg. Med. Chem. Lett.*, 6, 2283 (1996); K. Wisniewski, A. S. Koldziejczyk and B. Falkiewicz, *J. Pept. Sc.* 4, 1 (1998)].

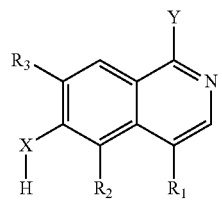

Formula III

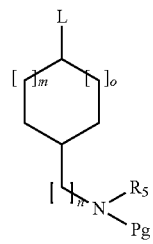

Formula IV

Alternatively, compounds of Formula IV wherein L represents a suitable leaving group, such as OMs, OTs, I, Br or Cl, can engage in a Williamson $S_N2$ mediated displacement reaction with a compound of Formula III in the presence of an appropriate base to yield a compound of Formula II.

Compounds of Formula III wherein X is S can be prepared from compounds of Formula III wherein X is O and Y is $NH_2$ carrying a protecting group such as Alloc, phthaloyl or benzoyl, by treatment with dimethylthiocarbamoyl chloride to give the corresponding O-ester (Newman, M. S. and Karnes, H. A. *J. Org. Chem.* 1966, 31, 3980) and subsequent Newman-Karnes conversion of the O-ester to the S-ester using microwave irradiation, followed by hydrolysis of the S-ester.

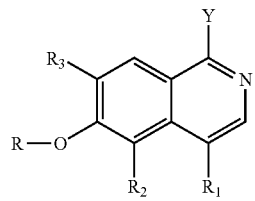

Formula V

Compounds of Formula III wherein X is O can be obtained from the demethylation of a compound of Formula V, wherein $R_1$-$R_3$, and Y have the previously given meaning and wherein R is methyl, by reaction with $BBr_3$ [J. F. W. McOmie and D. E. West, Org. Synth., Collect. Vol. V, 412 (1973)] or with EtSNa [A. S. Kende and J. P. Rizzi, Tetrahedron Lett., 22, 1779 (1981)]. Alternatively, a compound of Formula V wherein R is benzyl, can also be employed and the benzyl group removed using appropriate hydrogenation conditions.

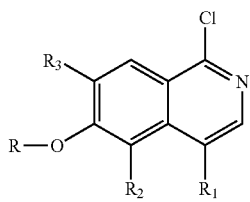

Formula VI

A compound of Formula VI is a suitable starting material for preparing compounds of Formula V. The chloro group of the compounds of Formula VI can be transformed directly into an amine group by heating the former with ammonia under pressure. Alternatively, the chloro group in compounds of Formula VI can be converted into a phenoxy group by reaction with phenol under alkaline conditions. Treatment of the phenoxy derivative with ammonium acetate affords the amine derivative of Formula V. Compounds of Formula V can also be obtained by treatment of a compound of Formula VI with sodium azide and subsequent reduction of the aryl azide with $PPh_3$.

Compounds of Formula VI can be obtained from compounds of Formula V, wherein Y is OH, by treatment with phosphoryl chloride.

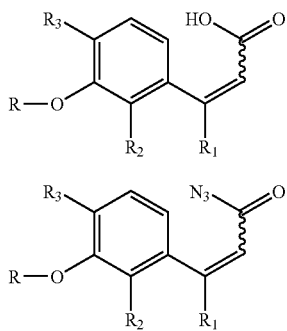

Formula VII

Formula VIII

Compounds of Formula V, wherein Y is OH, can be prepared from the corresponding cinnamic acids of Formula VII. The acids are converted to the acyl chlorides which are then transformed into the acyl azides of Formula VIII, which undergoes Curtius rearrangement on heating to afford an intermediate isocyanates, which on further heating results in an intramolecular ring closure reaction to give an isoquinolinone of Formula V.

Compounds of Formula I wherein X=NH can be prepared by conversion of the phenolic OH in compounds of Formula III to the corresponding bromide, which is subsequently coupled to an amine derivative of Formula IV (L=$NH_2$) by a palladium-catalyzed amination reaction (Wolfe J. P., Tomori H, Sadighi J. P., Yin, J and Buchwald S. L. *J. Org. Chem.* 2000, 65, 1158-1174).

The 6-substituted isoquinoline derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers.

Methods for asymmetric synthesis or chiral separation whereby the pure stereoisomers are obtained are well known in the art, e.g. synthesis with chiral induction or starting from commercially available chiral substrates, or separation of stereoisomers, for example using chromatography on chiral media or by crystallisation with a chiral counter-ion.

Pharmaceutically acceptable salts of the 6-substituted isoquinoline derivative of the invention may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid and methane sulfonic acid.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a 6-substituted isoquinoline derivatives according to general Formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration. A preferred route of administration is the oral route.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al, Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The compounds can be used in the treatment of Rho kinase mediated diseases, such as glaucoma, hypertension and atherosclerosis The compounds of the invention may be administered to humans in a sufficient amount and for a sufficient amount of time to alleviate the symptoms. Illustratively, dosage levels for humans can be in the range of 0.001-50 mg per kg body weight, preferably in a dosage of 0.01-20 mg per kg body weight.

The invention is illustrated by the following examples.

General:

The following abbreviations are used:

Eluent: x-y % solvent A in solvent B means that a gradient of the eluent of x % (v/v) of solvent A in solvent B to y % (v/v) of solvent A in solvent B was used.

EXAMPLE 1

Cis-6-(4-aminocyclohexyloxy)isoquinolin-1-ylamine

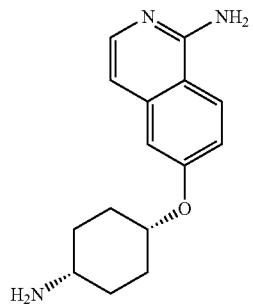

A: 6-Methoxy-isoquinoline-N-oxide hydrochloride

At ambient temperature 133 g of m-chloroperbenzoic acid (purity 75%) was added in portions to a stirred solution of 6-methoxy-isoquinoline [Hendricks, J. B. and Rodriguez, C., *J. Org. Chem.* 1983, 48, 3344-3346; 79.8 g; 500 mmol] in 1.2 L of dichloromethane. Stirring was continued for 3 hours and subsequently methanol (1 L) was added. The bulk was reduced to 700 ml after which 800 ml of a saturated solution of hydrogen chloride in diethyl ether was added. Dilution with 1.5 L of diethyl ether resulted in precipitation of yellow crystals, which were separated by filtration, washed with chilled diethyl ether and dried in vacuo to give 6-methoxy-isoquinoline-N-oxide hydrochloride (85 g, 80%), (+)-FAB-MS 176 [M+H-HCl]$^+$.

B: 1-Chloro-6-methoxyisooquinoline

6-Methoxyisoquinoline-N-oxide hydrochloride (85 g; 400 mmol) was carefully added in portions to phosphoryl chloride (550 mL) at a temperature of 90° C., after which the mixture was stirred for 6 h at 90° C. Excess of phosphoryl chloride was removed in vacuo. The remaining white solid was washed with water, filtered and dried in vacuo to give 1-chloro-6-methoxyisooquinoline (68 g, 88%), EI-MS: 193 [M]$^+$.

C: 6-Methoxy-1-phenoxyisoquinoline

To a mixture of 1-chloro-6-methoxyisoquioline (16.8 g, 87 mmol) and phenol (67 g) was added powdered potassium hydroxide (8.4 g). The mixture was heated under a nitrogen atmosphere to 140° C. for 3 h, allowed to cool to ambient temperature and subsequently diluted with 280 ml of 3N sodium hydroxide solution and 500 ml of dichloromethane. The organic layer was washed with 2N sodium hydroxide, water and brine, dried over magnesium sulphate and dried in vacuo to give 6-methoxy-1-phenoxyisoquinoline (21.3 g, 98%), ESI-MS: 251.8 [M+H]$^+$ D: 1-Amino-6-methoxyisoquinoline A mixture of 6-methoxy-1-phenoxyisoquinoline (21.3 g, 85 mmol) and ammonium acetate (55 g) was heated, under a nitrogen atmosphere, to 150° C. and stirred overnight. The mixture was allowed to cool to ambient temperature, after which 3 N sodium hydroxide (280 ml) was added with stirring. The thus obtained solution was extracted with ethyl acetate (2×300 ml) and the combined organic layers were extracted with 2N hydrochloric acid (100 ml). Subsequently, the pH of the aqueous layer was adjusted to 12 with 2 N sodium hydroxide. Extraction with ethyl acetate (300 ml) then afforded an organic layer, which was washed with brine (100 ml), dried (magnesium sulphate) and concentrated under reduced pressure to give 1-amino-6-methoxyisoquinoline (11 g, 75%), ESI-MS: 175.2 [M+H]$^+$ E: 1-Amino-6-hydroxyisoquinoline A solution of boron tribromide (18.2 ml, 370 mmol) in 20 ml dichloromethane was added dropwise to a stirred solution of 1-amino-6-methoxyisoquinoline (11.0 g, 63 mmol) in 150 ml of dichloromethane at 10° C. After stirring for 4 days at ambient temperature the reaction mixture was poured into ice and the pH was adjusted to 9 by adding concentrated aqueous ammonia. The precipitated material was collected by filtration and dried in vacuo to give 1-amino-6-hydroxyisoquinoline (8.9 g, 88%), EI-MS: 160 [M]$^+$ F: Trans-methanesulfonic acid 4-tert-butoxycarbonylaminocyclohexyl ester

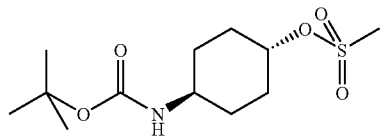

Methanesulfonyl chloride (135 µl, 1.74 mmol) was added to a cooled (ice bath, 0-4° C.), stirred solution of trans-(4-hydroxycyclohexyl)carbamic acid tert-butyl ester (0.25 g, 1.16 mmol) and triethylamine (243 µl, 1.74 mmol) in dichloromethane (10 ml). Following the addition the reaction was stirred at this temperature for 30 minutes before being allowed to warm to ambient temperature. After stirring at ambient temperature for 2 hours, aqueous sodium hydrogen carbonate (10 ml) was added, followed by vigorous stirring for 30 minutes. The reaction was diluted with dichloromethane (20 ml) and aqueous sodium hydrogen carbonate (20 ml) and after partitioning the organic phase was washed with water (20 ml), dried (magnesium sulphate) and evaporated to dryness under reduced pressure to yield methanesulfonic acid trans-4-tert-butoxycarbonylaminocyclohexyl ester (340 mg, 100%).

G: Cis-[4-(1-aminoisoquinolin-6-yloxy)cyclohexyl]carbamic acid tert-butyl ester

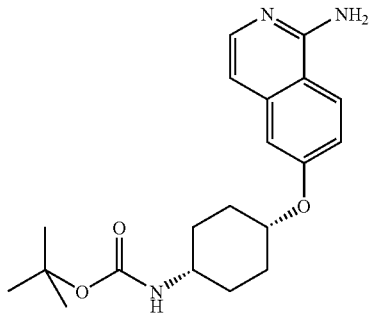

A suspension of 1-amino-6-hydroxyisoquinoline (0.08 g, 0.5mmol), methane-sulfonic acid trans-4-tert-butoxycarbonylaminocyclohexyl ester (176 mg) and 2-tert-butylimino-2-diethylamino-1,3-dimethyl-perhydro-1,3,2-diazaphosphorine on polystyrene (270mg, ~2.2 mmol/g loading) in acetonitrile (2ml) were heated at 120° C. over a period of 15 minutes using the microwave. The excess supported reagent was removed by filtration, washing with acetonitrile followed by methanol, and the filtrate evaporated to dryness under reduced pressure. Purification was achieved by prep-HPLC to give cis-[4-(1-aminoisoquinolin-6-yloxy)cyclohexyl]carbamic acid tert-butyl ester (14 mg).

EI-MS: m/z=358.5 $[M+H]^+$.

H: Cis-6-(4-amino-cyclohexyloxy)-isoquinolin-1-ylamine

A mixture of cis-[4-(1-aminoisoquinolin-6-yloxy)cyclohexyl]carbamic acid tert-butyl ester (14 mg) in dichloromethane (900 μl) and trifluoroacetic acid (100 μl) was stirred at ambient temperature for 3 h. The mixture was concentrated in vacuo then purified by prep-HPLC to give gave cis-6-(4-aminocyclohexyloxy)isoquinolin-1-ylamine (8.1 mg), EI-MS: m/z=258.5 $[M+H]^+$. $^1$H NMR (methanol D4) δ1.55-1.80 (6H, m), 2.05-2.15 (2H, m), 2.75-2.85 (1H, m), 4.65-4.75 (1H, obscured broad s), 6.88 (1H, d), 7.08-7.15 (2H, m), 7.64 (1H, d), 7.99 (1H, d).

EXAMPLE 2

Trans-6-(4-aminocyclohexyloxy)isoquinolin-1-ylamine

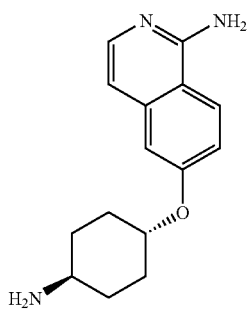

The title compound was prepared by the procedures as described in Example 1F 1G and 1H using the cis-(4-hydroxycyclohexyl)carbamic acid tert-butyl ester:

EI-MS: m/z=258.5 $[M+H]^+$.

EXAMPLE 3

Trans-6-(4-aminocyclohexylsulfanyl)isoquinolin-1-ylamine

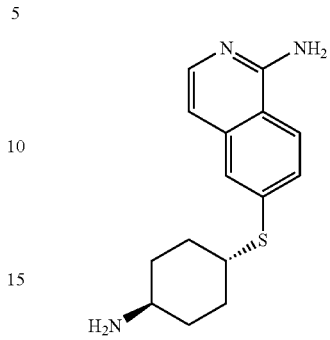

A: N-(6-Hydroxyisoquinolin-1-yl)-benzamide

Benzoic anhydride (10.27 g) was added to a solution of 1-aminoisoquinolin-6-ol (3.312 g) in pyridine (53 ml) at ambient temperature. The mixture was heated at 125° C. for 1 h, the pyridine was removed under reduced pressure and excess pyridine was removed by azeotroping with toluene (X2). Water was added and the mixture extracted with dichloromethane (X3), dried (sodium sulphate) and concentrated in vacuo to give a solid precipitate. Recrystallisation with dichloromethane-diethyl ether gave benzoic acid 1-benzylaminoisoqinolin-6-yl ester (6 g), EIMS: m/z=369.1 $[M+H]^+$.

A solution of NaOH (981 mg) in water $H_2O$ (65 ml) was added to a solution of benzoic acid 1-benzylaminoisoqinolin-6-yl ester (6 g) in methanol (65 ml) and tetrahydrofuran (65 ml). The mixture was stirred for 1.5 h at ambient temperature and then the organics were removed in vacuo. The mixture was diluted with water then extracted with ethyl acetate (x1). The aqueous phase was then acidified with dilute hydrochloric acid (pH~3.5). Addition of ethyl acetate resulted in a solid precipitate which was filtered and washed with cold MeOH then heptane to give N-(6-hydroxyisoquinolin-1-yl)benzamide (3.6 g), EIMS: m/z=265.1 $[M+H]^+$.

B: N-(6-Mercaptoisoquinolin-1-yl)benzamide

To a solution of N-(6-hydroxyisoquinolin-1-yl)benzamide (100 mg, 0.379 mmol), triethylamine (105 mL, 0.758 mmol) and pyridine (306 mL, 3.79 mmol) in anhydrous tetrahydrofuran (2 ml) was added N,N-dimethylthiocarbamoyl chloride (70 mg, 0.568 mmol) at 0° C., under nitrogen. The mixture was heated to 65° C. and stirred for 48 h. The organics were removed under reduced pressure and excess pyridine was removed by azeotroping with toluene (x 2). Saturated aqueous $NaHCO_3$ was added and the mixture was extracted with dichloromethane (x 2), dried (magnesium sulphate) and concentrated in vacuo to give a residue. Flash chromatography of the residue (eluent: 5-50% ethyl acetate in heptane) gave dimethylthiocarbamic acid O-(1-benzoylaminoisoquinolin-6-yl)ester (70 mg), EIMS: m/z=352.7 $[M+H]^+$.

A solution of the dimethylthiocarbamic acid O-(1-benzoylaminoisoquinolin-6-yl)ester (70 mg, ) in o-dichlorobenzene (3 ml) was irradiated in a microwave at 230° C. for 30 min. Flash chromatography of the mixture (eluent: 5-50% ethyl acetate in heptane) gave dimethylthiocarbamic acid S-(1-benzoylaminoisoquinolin-6-yl)ester (70 mg), EIMS: m/z=352.7 $[M+H]^+$.

A solution of NaOH (92 mg) in water $H_2O$ (1 ml) was added to a solution of dimethylthiocarbamic acid S-(1-benzoylaminoisoquinolin-6-yl)ester (70 mg) in MeOH (1 ml) and THF (1 ml). The mixture was stirred for 1 h at ambient temperature then for a further 1 h at 56° C. The organics were removed in vacuo then the mixture was diluted with water and acidified with dilute hydrochloric acid (pH~3.5). The mixture was extracted with ethyl acetate (X3), dried (sodium sulphate) and concentrated in vacuo to give a residue. Flash chromatography of the residue (eluent: 1-5% ethyl acetate in heptane) gave N-(6-mercaptoisoquinolin-1-yl)-benzamide (30 mg).

C: Trans-6-(4-aminocyclohexylsulfanyl)isoquinolin-1-ylamine

Potassium carbonate (160 mg) and methanesulfonic acid cis-4-tert-butoxycarbonylaminocyclohexyl ester (140 mg, 0.47 mmol) were added to a solution of N-(6-mercaptoisoquinolin-1-yl)benzamide residue in DMA (4 ml). The mixture was irradiated in a microwave at 120° C. for 600 s then concentrated in vacuo to give a residue. The residue was purified by preparative HPLC to give trans-[4-(1-benzoylaminoisoquinolin-6-ylsulfanyl)cyclohexyl]carbamic acid tert-butyl ester. Glacial acetic acid (1 ml) and 6M hydrochloric acid (2 ml) were added to the trans-[4-(1-benzoylaminoisoquinolin-6-ylsulfanyl)cyclohexyl]carbamic acid tert-butyl ester and the mixture was refluxed for 24 h. The mixture was then concentrated in vacuo to give a residue. The residue was loaded onto a pre-acidified SCX column using methanol and then eluted with 2M ammonia in methanol to give cude trans-6-(4-aminocyclohexylsulfanyl)isoquinolin-1-ylamine, which was further purified using prep-HPLC (9 mg), EIMS: m/z=274.5 [M+H]$^+$ The following compound was prepared by the procedure as described in 1F, 1G and 1H using the trans-4-tert-butoxycarbonylaminocyclohexyl ester:

EXAMPLE 4

Cis-6-(4-aminocyclohexylsulfanyl)isoquinolin-1-ylamine

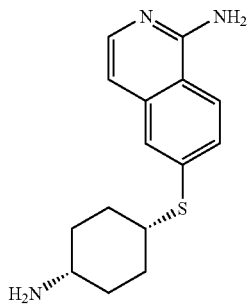

EIMS: m/z=274.3 [M+H]$^+$

EXAMPLE 5

Trans-6-(4-aminocyclohexyloxy)-7-methylisoquinolin-1-ylamine

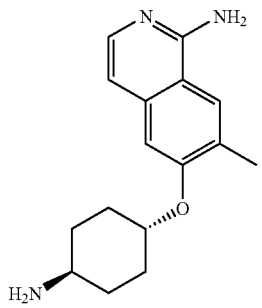

A: 1-Amino-7-methyl-isoquinolin-6-ol hydrobromide

A mixture of 3-methoxy-4-methylbenzaldehyde (19.3 g, 0.129 mol), carbomethoxy methylene triphenylphosphorane (51 g) in toluene (250 ml) was refluxed for 24 h. The mixture was quenched with aqueous ammonium chloride and extracted with ethyl acetate and concentrated in vacuo to give a residue. The residue was purified by flash chromatography using ethyl acetate-heptane (1:1) to give 3-(3-methoxy-4-methyl-phenyl)acrylic acid methyl ester (27 g, 0.126 mol). A mixture of 3-(3-methoxy-4-methylphenyl)acrylic acid methyl ester (27 g), sodium hydroxide (14 g), water (70 ml), methanol (140 ml) and tetrahydrofuran (70 ml) was refluxed at 50° C. for 1 h. The mixture was concentrated in vacuo and then water added. The mixture was filtered and 5 M HCl was added until precipitation occurred. The mixture was filtered and the solid precipitate washed with water and dried in-vacuo to give 3-(3-methoxy-4-methylphenyl)acrylic acid (23.5 g, 0.122 mol).

Toluene (750 ml) and thionyl chloride (11 ml) were subsequently added to 3-(3-methoxy-4-methylphenyl)acrylic acid (20 g, 0.104 mol) at room temperature. The suspension was refluxed for 2 h while vigorously stirring to give a clear slightly yellow solution. The reaction mixture was concentrated in vacuo, then toluene added and the mixture re-concentrated in vacuo to give 3-(3-methoxy-4-methylphenyl)acryloyl chloride for use in the next step.

The 3-(3-methoxy-4-methylphenyl)acryloyl chloride was dissolved in acetone (800 ml). The resulting solution was added slowly (15 min) at 0° C. to a mixture of sodium azide (13 g) in water (100 ml) and acetone (100 ml) while vigorously stirring and cooling with an ice-bath. After addition was complete the reaction mixture was stirred at 0° C. for 90 minutes while vigorously stirring. The reaction mixture was then poured out on ice-water (300ml). After stirring for 15 minutes the mixture was filtered and the solid residue washed with excess water. The remaining solid residue was dissolved in dichloromethane (45 ml). The liberated water was removed with a separatory funnel. The dichloromethane layer was dried with Na$_2$SO$_4$ and filtered to give a dichloromethane solution of 3-(3-methoxy-4-methylphenyl)acryloyl azide for immediate use in the next step.

The dichloromethane azide solution was added in portions (Carefully !) using a dropping funnel to preheated diphenyl ether (50 ml) at 150° C., while gently stirring, in a three-necked roundbottomed flask, equiped with a Dean-Stark trap. During the addition nitrogen gas evolution takes place under formation of the isocyanate. The added dichloromethane is evaporated and collected with the Dean-Stark trap. After the addition was complete (~30 min) and no gas evolution observed, the mixture was heated to reflux (~250° C.) while stirring (At ~200° C. no more dichloromethane is evaporated and the Dean-Stark trap is removed quickly). The reaction mixture is kept at ~250° C. for 1 h then cooled to 125° C. and poured out in a mixture of acetone and heptane (1:10). A solid precipitated and this was filtered and dried in vacuo to give 6-methoxy-7-methyl-2H-isoquinolin-1-one (12 g, 63.49 mmol).

A suspension of 6-methoxy-7-methyl-2H-isoquinolin-1-one (5 g, 26.45 mmol) was treated at room temperature with phosphorus oxychloride (22 ml). The mixture was heated at 100° C. for 1 h with stirring then concentrated in vacuo to give a residue. Toluene was added to the residue which was further concentrated in-vacuo to give a residue which was taken up in toluene and slowly added to saturated aqueous sodium carbonate. The toluene layer was then separated. The aqueous layer was further mixed and extracted with toluene. The combined toluene layers were dried (MgSO$_4$) and concentrated in vacuo to give a residue. The residue was triturated with diethyl ether then filtered and dried in vacuo to give 1-chloro-6-methoxy-7-methyl-isoquinoline (4 g, 19.32 mmol).

A mixture of 1-chloro-6-methoxy-7-methyl-isoquinoline (9 g, 43.48 mol), phenol (16.3 g), potassium hydroxide (9.45 g) and xylene (100 ml) was refluxed for 4 days. The reaction mixture was poured out into aqueous sodium hydroxide (4 M) and the xylene layer separated. The aqueous layer was extracted twice with toluene. The combined organic layers were dried ($Na_2SO_4$) and concentrated in vacuo to give a residue. The residue was purified by flash chromatography using dichloromethane gave 6-methoxy-7-methyl-1-phenoxyisoquinoline (9 g, 33.96 mmol).

A mixture of the crude 6-methoxy-7-methyl-1-phenoxyisoquinoline (9 g, 33.96 mmol) and ammonium acetate (26 g) was melted with stirring at 170° C. for 5 h. The mixture was partitioned between aqueous sodium hydroxide (2 M) and ethyl acetate. The phases were separated and the organic phase extracted with dilute aqueous hydrochloric acid. The acidic aqueous phase was neutralized to pH 12 using sodium hydroxide (2M), extracted with ethyl acetate, dried ($MgSO_4$) then dried in vacuo to give 6-methoxy-7-methylisoquinolin-1-ylamine (5.11 g, 27.18 mmol).

A mixture of 6-methoxy-7-methylisoquinolin-1-ylamine (5.11 g, 27.18 mmol) and 48% aqueous hydrobromic acid (150 ml) was heated at 125° C. for 2 days. The mixture was concentrated in vacuo and triturated with diethyl ether, dried in vacuo to give 1-amino-7-methyl-isoquinolin-6-ol hydrobromide (5 g), EIMS: m/z=175.1 [M+H]$^+$. $^1$H NMR (DMSO-D6) δ7.06 (1H, d), 7.16 (1H, d), 7.25 (1H, dd), 7.56 (1H, d), 8.44 (1H, dd), 8.66 (2H, broad s), 11.05 (1H, s), 12.45 (1H, s).

B: Trans-6-(4-aminocyclohexyloxy)-7-methylisoquinolin-1-ylamine 1-amino-7-methylisoquinolin-6-ol hydrobromide (100 mg, 0.57 mmol), potassium carbonate (78 mg, 0.57 mmol) and methanesulfonic acid cis-4-tert-butoxycarbonyl-aminocyclohexyl ester (166 mg, 0.57 mmol) were mixed with N,N-dimethylformamide (3 ml). The mixture was heated in a microwave at 100° C. for 15 min. The mixture was diluted with water, acidified with glacial acetic acid, diluted with methanol and loaded onto a pre-acidified SCX cartridge. The crude product obtained after elution with 2M ammonia in methanol was purified by prep-HPLC to give trans-6-(4-aminocyclohexyloxy)-7-methylisoquinolin-1-ylamine (8 mg), EI-MS: m/z=272.7 [M+H]$^+$.

The following compound was prepared by the procedure described above using the appropriately synthesised mesylate.

EXAMPLE 6

Cis-6-(4-aminocyclohexyloxy)-7-methyylisoquinolin-1-ylamine

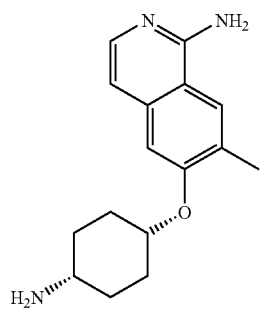

EI-MS: m/z=272.7 [M+H]$^+$.

EXAMPLE 7A

Cis-6-(4-aminocyclohexyloxy)-2H-isoquinolin-1-one (reference example)

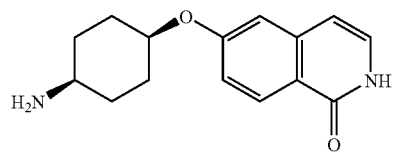

A: 6-Hydroxy-2H-isoquinolin-1-one

The 1-chloro-6-methoxyisoquinoline was prepared according to Example 1A or from 3-methoxybenzaldehyde using the same procedure as in Example 5A. The 1-chloro-6-methoxy-7-methylisoquinoline was then demethylated according Example 1E to afford 1-chloro isoquinolin-6-ol.

1-Chloroisoquinolin-6-ol (5 g, 27.84 mmol) was mixed with hydrochloric acid (5M, 40 ml) and heated at 180° C. for 40 minutes under microwave conditions. The mixture was allowed to cool and then filtered. The brown solid was washed with Diethyl ether and dried in the oven at 50° C. in vacuo to give 6-Hydroxy-2H-isoquinolin-1-one, 4.45 g (98%), EI-MS: m/z=162.4 [M+H]$^+$. $^1$H NMR (Methanol-D4) δ6.80 (1H, d), 7.01 (1H, d), 7.10 (1H, dd), 7.25 (1H, d), 8.22 (1H, d).

B: Methanesulfonic acid trans-4-tert-butoxycarbonylaminocyclohexyl ester

Methanesulfonyl chloride (135 μl, 1.74 mmol) was added to a cooled (ice bath, 0-4° C.), stirred solution of (trans-4-hydroxycyclohexyl)carbamic acid tert-butyl ester (0.25 g, 1.16 mmol) and triethylamine (243 μl, 1.74 mmol) in dichloromethane (10 ml). Following the addition the reaction was stirred at this temperature for 30 minutes before being allowed to warm to ambient temperature. After stirring at ambient temperature for 2 hours, aqueous sodium hydrogen carbonate (10 ml) was added, followed by vigorous stirring for 30 minutes. The reaction was diluted with dichloromethane (20 ml) and aqueous sodium hydrogen carbonate (20 ml) and after partitioning the organic phase was washed with water (20 ml), dried ($MgSO_4$) and evaporated to dryness under reduced pressure to yield methanesulfonic acid trans-4-tert-butoxycarbonylaminocyclohexyl ester (340 mg, 100%).

C: 6-(Cis-4-aminocyclohexyloxy)-2H-isoquinolin-1-one

A suspension of 6-Hydroxy-2H-isoquinolin-1-one (0.1 g, 0.62 mmol) and potassium carbonate (0.13 g, 0.93 mmol) in DMF (2.5 ml) was heated to 110° C. and a solution of methanesulfonic acid trans-4-tert-butoxycarbonylaminocyclohexyl ester (0.27 g, 0.93 mmol) in DMF (1.5 ml) was added dropwise. Heating was continued at 110° C. for 16 hours and the solvent removed in vacuo. The residue was taken up in chloroform/isopropanol (3:1) and washed with 1M NaOH. The organics were collected through a hydrophobic frit and concentrated to afford crude product. The residue was purified by prep-H PLC to give cis-[4-(1-oxo-1,2-dihydroisoquinolin-6-yloxy)cyclohexyl]carbamic acid tert-butyl, EI-MS: m/z=359.1 [M+H]$^+$. A mixture of the above cis-[4-(1-Oxo-1,2-dihydroisoquinolin-6-yloxy)cyclohexyl]carbamic acid tert-butyl ester in dichloromethane (0.9 ml) and trifluoroacetic acid (0.1 ml) was stirred at ambient temperature for 1 hour. The mixture was concentrated in vacuo then purified by ion exchange chromatography to give cis-6-(4-aminocyclohexyloxy)-2H-isoquinolin-1-one (3.1 mg), EI-MS: m/z=259.1 [M+H]$^+$.

The following compounds of the invention were prepared by the procedure as described for reference example 7A using the appropriate Boc-protected amino alcohol:

EXAMPLE 7B 6-(4-Aminomethylcyclohexyloxy)-2H-isoquinolin-1-one

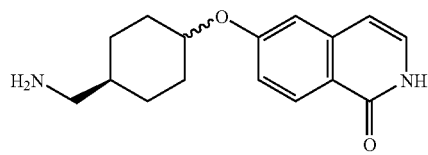

EI-MS: m/z=273.5 [M+H]$^+$.

EXAMPLE 7C (1R,3R)-6-(3-methylaminomethyl-cyclopentyloxy)-2H-isoquinolin-1-one

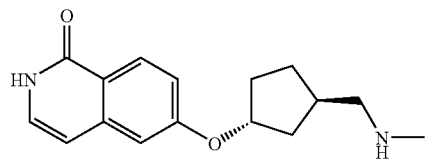

ESI-MS: m/z=273.1

EXAMPLE 7D (1S,3R)-6-(3-methylaminomethyl-cyclopentyloxy)-2H-isoquinolin-1-one

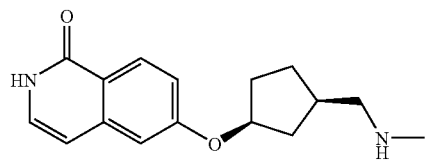

ESI-MS: m/z=273.1

EXAMPLE 7E (1R,3S)-6-(3-methylaminomethyl-cyclopentyloxy)-2H-isoquinolin-1-one

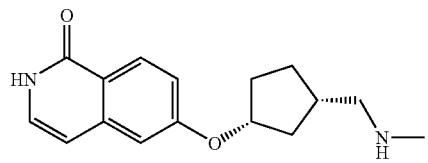

ESI-MS: m/z=273.1

EXAMPLE 7F (1S,3S)-6-(3-methylaminomethyl-cyclopentyloxy)-2H-isoquinolin-1-one

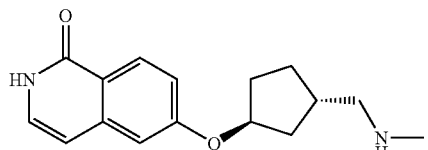

ESI-MS: m/z=273.1

EXAMPLE 7G (1S,3S)-6-(3-ethylaminomethyl-cyclopentyloxy)-2H-isoquinolin-1-one

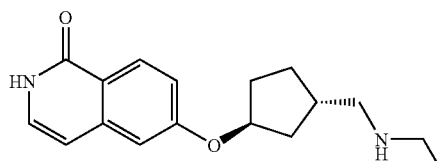

ESI-MS: m/z=287.2 [M+H]$^+$.

EXAMPLE 7H (1S,3R)-6-[3-(cyclopropylaminomethyl)cyclopentyloxy]-2H-isoquinolin-1-one

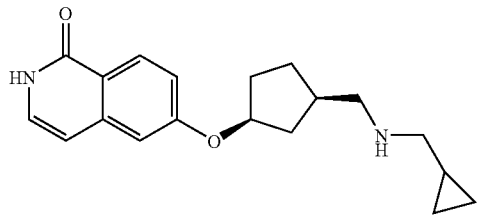

ESI-MS: m/z=313.2 [M+H]$^+$.

EXAMPLE 7I (1R,3R)-6-(3-ethylaminomethyl-cyclopentyloxy)-2H-isoquinolin-1-one

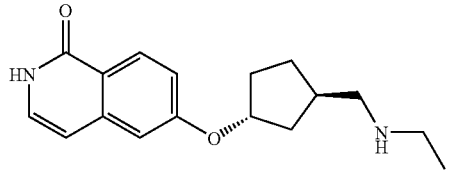

ESI-MS: m/z=287.2 [M+H]$^+$.

EXAMPLE 7J (1S,3R)-6-(3-ethylaminomethyl-cyclopentyloxy)-2H-isoquinolin-1-one

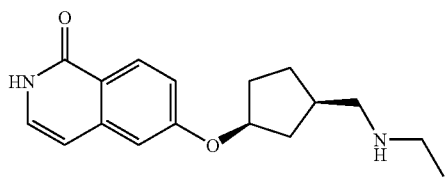

ESI-MS: m/z=287.2 [M+H]$^+$.

EXAMPLE 7K (1R,3S)-6-(3-ethylaminomethyl-cyclopentyloxy)-2H-isoquinolin-1-one

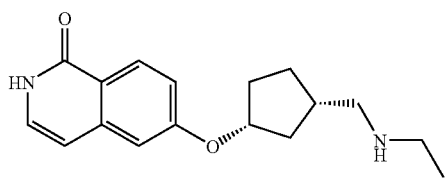

ESI-MS: m/z=287.2 [M+H]$^+$.

EXAMPLE 7L 6-(4-cyclopropylmethylaminomethyl-cyclohexyloxy)-2H-isoquinolin-1-one

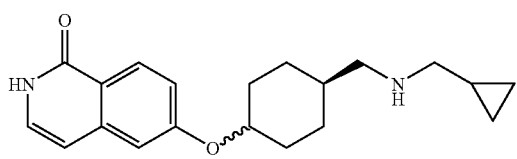

ESI-MS: m/z=327.3 [M+H]$^+$.

EXAMPLE 7M 6-(4-ethylaminomethyl-cyclohexyloxy)-2H-isoquinolin-1-one

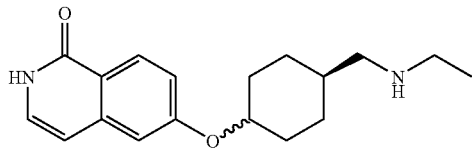

ESI-MS: m/z=301.1 [M+H]$^+$.

EXAMPLE 8

Trans-6-(4-methylaminocyclohexyloxy)-2H-isoquinolin-1-one (reference example)

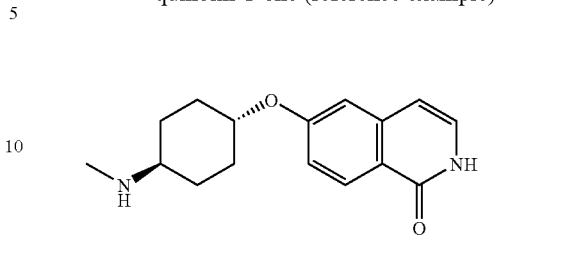

A: Cis-4-methylaminocyclohexanol

A 2M solution of lithium aluminium hydride in THF (4.6 ml) was added dropwise to a solution of cis-(4-hydroxycyclohexyl)carbamic acid tert-butyl ester (1 g, 4.6 mmol) in THF (5 ml) stirring at ambient temperature. After stirring for 30 minutes the mixture was heated at reflux for 16 hours. After allowing to cool, water (0.35 ml) followed by 2N sodium hydroxide (0.35 ml) and water (0.35 ml) were carefully added. The white precipitate was removed by filtration and the filtrate concentrated under reduced pressure. The remaining aqueous was diluted with water and neutralised by dropwise addition of 4N hydrochloric acid. The aqueous was slowly passed through an ion exchange column (SCX, 10 g) and after washing with methanol the product was eluted with 2M ammonia in Methanol solution. Fractions combined and concentrated under reduced pressure to afford cis-4-methylaminocyclohexanol (455 mg, 76%).

B: Cis-(4-hydroxycyclohexyl)methylcarbamic acid tert-butyl ester

To a solution of cis-4-methylamino-cyclohexanol (450 mg, 3.48 mmol) in methanol (30 ml) was added di-tert-butyl dicarbonate (840 mg, 3.83 mmol) and sodium hydrogen carbonate (1.75 g, 20.9 mmol). The resultant suspension was sonicated at 40° C. for 3 hours and then the solvent removed in vacuo to give a residue that was partitioned between water and dichloromethane. The organic layer was separated and washed with saturated brine and then water before drying (MgSO$_4$) and concentrating under reduced pressure to afford cis-(4-hydroxycyclohexyl)methylcarbamic acid tert-butyl ester.

C: Methanesulfonic acid cis-4-(tert-butoxycarbonylmethylamino)cyclohexyl ester

Methanesulfonyl chloride (290 µl, 3.72 mmol) was added to a cooled (ice bath, 0-4° C.), stirred solution of cis-(4-hydroxycyclohexyl)methylcarbamic acid tert-butyl ester (710 mg, 3.10 mmol) and triethylamine (520 µl, 3.72 mmol) in dichloromethane (15 ml). Following the addition the reaction was stirred at this temperature for 30 minutes before being allowed to warm to ambient temperature. After stirring at ambient temperature for 2 hours, aqueous sodium hydrogen carbonate (15 ml) was added, followed by vigorous stirring for 30 minutes. The reaction was diluted with dichloromethane (30 ml) and aqueous sodium hydrogen carbonate (30 ml) and after partitioning the organic phase was collected and evaporated to dryness under reduced pressure to yield methane-sulfonic acid cis-4-(tert-butoxycarbonylmethylamino)cyclohexyl ester (930 mg, 98%).

D: Trans-methyl[4-(1-oxo-1,2-dihydroisoquinolin-6-yloxy)cyclohexyl]carbamic acid tert-butyl ester suspension of 6-Hydroxy-2H-isoquinolin-1-one (410 mg, 2.52 mmol) and potassium carbonate (420 mg, 3.03 mmol) in DMF (7 ml) was heated to 110° C. and a solution of methanesulfonic acid cis-4-(tert-butoxycarbonylmethylamino)cyclohexyl ester (930 mg, 3.03 mmol) in DMF (3 ml) was added dropwise. Heating was continued at 110° C. for 16 hours and the solvent removed in vacuo. The residue was taken up in chloroform/isopropanol (3:1) and washed with aqueous sodium hydrogen carbonate. The organics were collected through a hydrophobic frit and concentrated to afford crude product. The residue was purified by flash chromatography on silica (eluent: dichloromethane followed by 2M ammonia in methanol) to give trans-methyl[4-(1-oxo-1,2-dihydroisoquinolin-6-yloxy)cyclohexyl]carbamic acid tert-butyl ester (400 mg, 42%), EI-MS: m/z=373.1 [M+H]$^+$.

E: Trans-6-(4-methylaminocyclohexyloxy)-2H-isoquinolin-1-one

A solution of trans-methyl[4-(1-oxo-1,2-dihydroisoquinolin-6-yloxy)cyclohexyl]-carbamic acid tert-butyl ester (400 mg, 1.07 mmol) in dichloromethane (9 ml) and trifluoroacetic acid (1 ml) was stirred at ambient temperature for 1 hour. The mixture was concentrated in vacuo then purified by ion exchange chromatography to give trans-6-(4-methylaminocyclohexyloxy)-2H-isoquinolin-1-one, EI-MS: m/z=273.4 [M+H]$^+$.

EXAMPLE 9A

Trans-6-(4-dimethylaminocyclohexyloxy)-2H-isoquinolin-1-one (reference example)

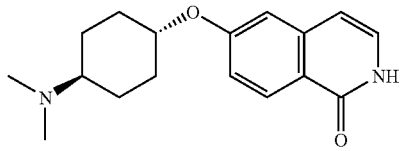

A couple of drops of glacial acetic acid were added to a solution of trans-6(4-methylaminocyclohexyloxy)-2H-isoquinolin-1-one (Example 12; 25 mg, 92 μmol) and formaldehyde (40 μL) in acetonitrile (1 ml). The mixture was stirred for 20 minutes and then sodium triacetoxyborohydride (100 mg) was added. The mixture was stirred at ambient temperature for 16 hours then concentrated in vacuo. The residue was partitioned between chloroform/isopropanol (3:1) and aqueous sodium hydrogen carbonate. The organic layer was separated then concentrated to give a residue that was purified by prep-HPLC to give trans-6(4-dimethylaminocyclohexyloxy)-2H-isoquinolin-1-one, EI-MS: m/z=287.3 [M+H]$^+$.

The following compounds were prepared by the same procedures as described above for reference examples 8 and 9A using the appropriate amine:

EXAMPLE 9B (1R,3S)-6-(3-dimethylaminomethyl-cyclopentyloxy)-2H-isoquinolin-1-one

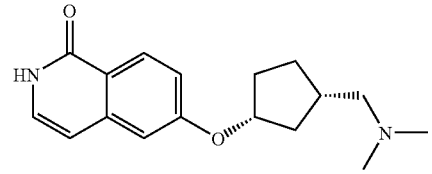

ESI-MS: m/z=287.2 [M+H]$^+$.

EXAMPLE 9C (1R,3S)-6-[3-((cyclopropylmethylmethylamino)-methyl)-cyclopentyloxy]-2H-isoquinolin-1-one

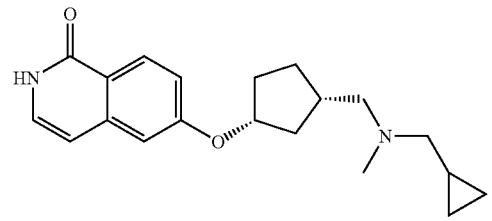

ESI-MS: m/z=327.3 [M+H]$^+$.

EXAMPLE 9D (1R,3S)-6-[3-((ethylmethylamino)-methyl)-cyclopentyloxy]-2H-soquinolin-1-one

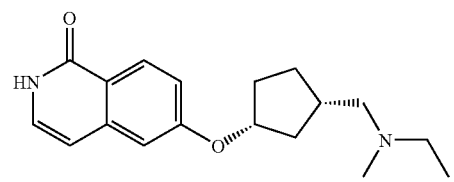

ESI-MS: m/z=301.3 [M+H]$^+$.

EXAMPLE 9E (1R,3S)-6-(3-(diethylaminomethyl-cyclopentyloxy)-2H-isoquinolin-1-one

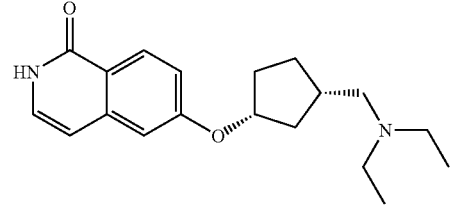

ESI-MS: m/z=315.2 [M+H]$^+$.

EXAMPLE 9F (1R,3S)-6-(3-(propylmethylaminomethyl-cyclopentyloxy)-2H-isoquinolin-1-one

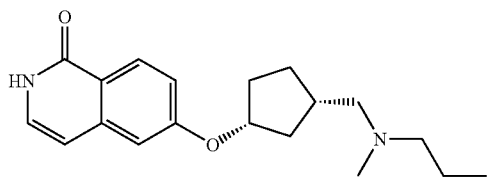

ESI-MS: m/z=315.3 [M+H]$^+$.

EXAMPLE 9G (1S,3S)-6-(3-(dimethylaminomethyl-cyclopentyloxy)-2H-isoquinolin-1-one

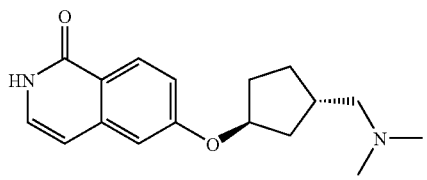

ESI-MS: m/z=287.2 [M+H]$^+$.

EXAMPLE 9H (1S,3S)-6-(3-(propylmethylaminomethyl-cyclopentyloxy)-2H-isoquinolin-1-one

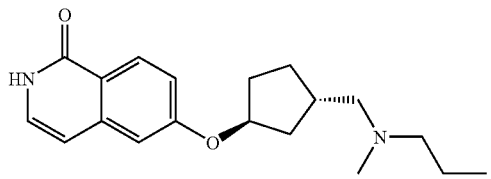

ESI-MS: m/z=315.3 [M+H]$^+$.

EXAMPLE 10

(1R,3S)-6-(3-aminomethylcyclopentyloxy)-2H-isoquinolin-1-one

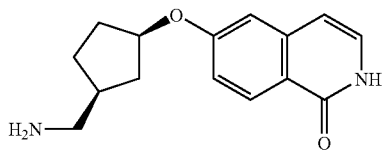

Di-tert-butyldicarbonate (260 mg, 1.2 mmol) was added to a solution of (1S, 3S) 3-aminomethylcyclopentanol (100 mg, 1 mmol) in dichloromethane (1.5 ml) and triethylamine (415 μL, 3 mmol) at ~5° C. The mixture was warmed to ambient temperature then stirred overnight. Water was added, the mixture was diluted with dichloromethane and the organic phase separated and concentrated in vacuo to give (1S, 3R)-(3-hydroxycyclopentylmethyl)carbamic acid tert-butyl ester. Without further purification the residue was dissolved in dichloromethane (2 ml) and triethylamine (182 μL). Methane sulphonyl chloride (102 μL) was added at ~5° C. and the mixture was heated to ambient temperature and stirred for 3 days. Saturated aqueous NaHCO$_3$ was added, the mixture was diluted with dichloromethane and the organic phase separated and concentrated in vacuo to give methanesulfonic acid (1R,3S)-3-(tert-butoxycarbonylaminomethyl)cyclopentyl ester, which was used in the next step without further purification.

A solution of the methanesulfonic acid (1R,3S)-3-(tert-butoxycarbonyl-aminomethyl)cyclopentyl ester in N,N-dimethylformamide (2 ml) was added over 15 minutes to a stirred solution of 6-hydroxy-2H-isoquinolin-1-one (161 mg, 1 mmol) and potassium carbonate (276 mg) in N,N-dimethylformamide (2 ml) at 100° C. The mixture was stirred at 90° C. for 4 h then allowed to cool to ambient temperature and stirred overnight. Saturated aqueous NaHCO$_3$ was added, the mixture was extracted with chloroform: isopropanol (3:1) and the organic phase concentrated in vacuo to give a residue. A dichloromethane: trifluoroacetic acid solution (3:1, 3 ml) was added to the residue and the resultant mixture stirred for 3.5 h, then concentrated in vacuo to give a residue. The residue was loaded onto a pre-acidified SCX column using methanol and eluted with 2M ammonia in methanol to afford crude (1R, 3S)-6-(3-aminomethylcyclopentyloxy)-2H-isoquinolin-1-one, which was purified by prep-HPLC (2 mg); EI-MS: m/z=259.1 [M+H]$^+$.

The following compounds were prepared by the procedure as described in Example 10 using the appropriate mesylate and 6-hydroxy-2H-isoquinolin-1-one:

EXAMPLE 11A (1S, 3R)-6-(3-aminomethylcyclopentyloxy)-2H-isoquinolin-1-one

EI-MS: m/z=259.0 [M+H]$^+$.

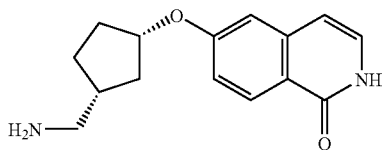

EXAMPLE 11B (1R, 3R)-6-(3-aminomethylcyclopentyloxy)-2H-isoquinolin-1-one

EI-MS: m/z=259.0 [M+H]$^+$.

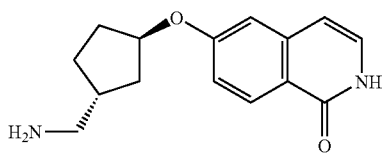

EXAMPLE 11C (1S, 3S)-6-(3-aminomethylcyclopentyloxy)-2H-isoquinolin-1-one

EI-MS: m/z=259.1 [M+H]⁺.

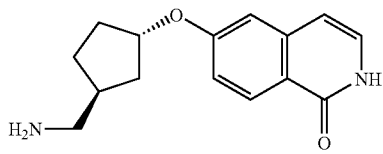

EXAMPLE 11D (1S, 3S)-6-(3-aminocyclopentyloxy)-2H-isoquinolin-1-one

EI-MS: m/z=245.3 [M+H]⁺.

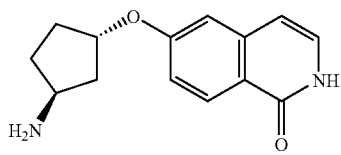

EXAMPLE 11E (1R, 3R)-6-(3-aminocyclopentyloxy)-2H-isoquinolin-1-one

EI-MS: m/z=245.3 [M+H]⁺.

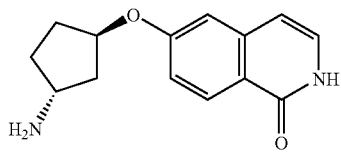

EXAMPLE 12

In-vitro Determination of Inhibitory Activity of Compounds of the Invention on Recombinant Human ROCK-1.

To a 384 well microtitre plate is added 5µl of a 250µM solution of test compound in assay buffer (20 mM Hepes pH7.4, 0.01% tween) with 4% dimethylsulfoxide (DMSO), plus 5 µl of a mixture containing 100 nM fluorescein-labelled peptide (AKRRRLSSLRAK-fluorescein from the Peptide Institute, Japan), 20 µM ATP, 10mM MgCl₂ diluted in assay buffer containing 2 mM dithiothreitol. 10 µl of a 0.1 ng/µl solution of recombinant human ROCK-I in assay buffer containing 2 mM dithiothreitol, is then added to each well, yielding a final test compound concentration of 10 µM. Following a one hour incubation at room temperature in the dark, enzyme activity is detected by adding 60 µl of IMAP binding reagent (Molecular Devices) to each well. The plate is incubated for a further 30 minutes at room temperature in the dark and the resulting change in fluorescence polarisation is measured on the Analyst HT (Molecular Devices) at an excitation wavelength of 485 nM and emission wavelength of 530 nM. Percentage enzyme activity is calculated by comparison of this activity to that of a solution containing 30 µM Y-27632 from Tocris (generates maximum inhibition of ROCK-I activity). Compounds are subsequently subjected to a dose response curve analysis in order to determine $IC_{50}$ values for active compounds (where $IC_{50}$ is the concentration of test compound causing 50% inhibition of the enzymatic activity). Most compounds of the invention are characterized by an $IC_{50}$ of greater than 5. Preferred compounds of the invention, such as those described in examples 4, 7B, 10, 11A, 11B, 11C, 11D and 11E, have $pIC_{50}$ of greater than 6.5.

EXAMPLE 13

In-vitro Determination of the Monocyte Migration Inhibitory Activity of Compounds of the Invention Human monocytic cells (THP-1) were suspended in migration medium (RPMI 1640 containing 0.1% BSA) at a concentration of 2×10⁶ cells/ml in the presence and absence of inhibitory test compound. The cell suspension was then incubated for 30 min at 37° C. A solution of human Monocyte Chemotactic Protein 1 (MCP-1) at a concentration of 10 ng/ml in migration medium was then added to the lower chamber of the QCMTM Chemotaxis 5 µM 96-Well Cell Migration Kit (ECM512, Chemicon International). Following the introduction of the migration insert and a 10min pre-equilibration step, 100 µl of the cell suspension was then added to the upper chamber and the kit incubated for 4hrs at 37° C. under 5% carbon dioxide. Blank and Basal Migratory wells were also included, containing no cells and no MCP-1, respectively. The number of migratory cells was determined via the application of a lysis buffer and nucleic acid sensitive fluorescent dye (CyQuant GR dye, Molecular Probes). Fluorescence was then determined using the FlexStation Plate Reader. Percentage migration inhibition was calculated using the following equation:

Specific Migration Inhibition (%)=(1-{(Migrated cells in the presence of test compound-Basal Migrated Cells)/(Migrated cells in the absence of test compound-Basal Migrated Cells)})×100

The invention claimed is:

1. A 6-substituted isoquinoline compound having the Formula I

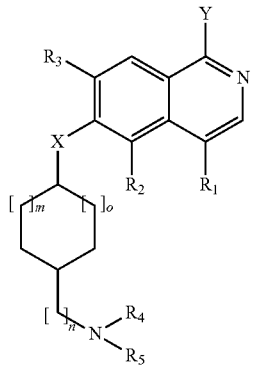

Formula I wherein

X is O, S or NH;

Y is OH or $NH_2$;

m is 0, 1 or 2;

n is 0 or 1;

o is 0 or 1

$R_1$ is H, when Y is $NH_2$; or $R_1$ is H, $(C_{1-4})$alkyl or halogen, when Y is OH;

$R_2$ and $R_3$ are independently H, $(C_{1-4})$alkyl or halogen;

$R_4$ is H or $(C_{1-6})$alkyl, optionally substituted with halogen, $(C_{3-7})$cycloalkyl, $(C_{6-10})$aryl or a saturated 5- or 6-membered heterocyclic ring comprising 1-3 heteroatoms independently selected from O, S and N, the $(C_{6-10})$aryl and heterocyclic ring being optionally substituted with $(C_{1-4})$alkyl, $(C_{1-4})$alkyloxy or halogen;

$R_5$ is H or $(C_{1-4})$alkyl;

or a pharmaceutically acceptable salt thereof, with the proviso that the compounds of Formula I wherein X is O, Y is OH, n is 0 and m+o =2 are excluded.

2. The 6-substituted isoquinoline compound of claim 1, wherein Y is OH.

3. The 6-substituted isoquinoline compound of claim 1, wherein X is O.

4. The 6-substituted isoquinoline compound of claim 1, wherein $R_1$ and $R_3$ are independently H, methyl or halogen, and $R_2$ is H.

5. The 6-substituted isoquinoline compound of claim 1, wherein n is 0.

6. The 6-substituted isoquinoline compound which is selected from:

(1S, 3R)-6-(3-aminomethylcyclopentyloxy)-2H- isoquinolin- 1-one;

6-(4-aminomethylcyclohexyloxy)-2H-isoquinolin- 1-one;

(1R, 3R)-6-(3-aminomethylcyclopentyloxy)-2H- isoquinolin- 1-one;

(1R, 3S)-6-(3-aminomethylcyclopentyloxy)-2H-isoquinolin- 1-one;

(1S, 3S)-6-(3-aminocyclopentyloxy)-2H-isoquinolin- 1-one;

(1R, 3R)-6-(3-aminocyclopentyloxy)-2H-isoquinolin- 1-one;

cis-6-(4-aminocyclohexylsulfanyl)isoquinolin-1-ylamine;

(1S, 3S)-6-(3- aminomethylcyclopentyloxy)-2H-isoquinolin-1-one; or a pharmaceutically acceptable salt thereof.

7. A pharmaceutical composition comprising a 6-substituted isoquinoline compound of claim 1, or a pharmaceutically acceptable salt thereof, in admixture with pharmaceutically acceptable auxilliaries.

8. A pharmaceutical composition comprising a 6-substituted isoquinoline compound of claim 6, or a pharmaceutically acceptable salt thereof, in admixture with pharmaceutically acceptable auxilliaries.

9. A method for the treatment of a ROCK-I-related disorder in a subject in need of treatment, the method comprising administering an effective amount of the compound according to claim 1, or a pharmaceutically acceptable salt thereof.

10. The method according to claim 9, wherein the ROCK-I-related disorder is selected from the group consisting of glaucoma, hypertension and atherosclerosis.

11. A method for the treatment of a ROCK-I-related disorder in a subject in need of treatment, the method comprising administering an effective amount of the compound according to claim 6, or a pharmaceutically acceptable salt thereof.

12. The method according to claim 11, wherein the ROCK-I-related disorder is selected from the group consisting of glaucoma, hypertension and atherosclerosis.

* * * * *